(12) United States Patent
Fujimoto et al.

(10) Patent No.: US 10,338,023 B2
(45) Date of Patent: Jul. 2, 2019

(54) TEMPERATURE AND HUMIDITY SENSOR

(71) Applicant: Murata Manufacturing Co., Ltd., Nagaokakyo-shi, Kyoto-fu (JP)

(72) Inventors: Katsumi Fujimoto, Nagaokakyo (JP); Hiroshi Shiraki, Nagaokakyo (JP); Keisuke Yamamoto, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 457 days.

(21) Appl. No.: 15/041,262

(22) Filed: Feb. 11, 2016

(65) Prior Publication Data

US 2016/0161435 A1 Jun. 9, 2016

Related U.S. Application Data

(63) Continuation of application No. PCT/JP2014/070702, filed on Aug. 6, 2014.

(30) Foreign Application Priority Data

Aug. 13, 2013 (JP) ................................ 2013-168039

(51) Int. Cl.
*G01N 27/22* (2006.01)
*G01K 7/16* (2006.01)
*G01K 7/20* (2006.01)

(52) U.S. Cl.
CPC ............. *G01N 27/223* (2013.01); *G01K 7/16* (2013.01); *G01K 7/203* (2013.01)

(58) Field of Classification Search
CPC ......... G01N 27/223; G01K 7/16; G01K 7/203
See application file for complete search history.

(56) References Cited

U.S. PATENT DOCUMENTS 4,442,422 A * 4/1984 Murata ................ G01N 27/121
324/696
4,491,784 A * 1/1985 Flora .................... G01N 27/223
324/668

(Continued)

FOREIGN PATENT DOCUMENTS

JP 58-70153 A 4/1963
JP 61-14556 A 1/1986

(Continued)

OTHER PUBLICATIONS

International Search Report for PCT/JP2014/070702, dated Sep. 9, 2014.
Written Opinion for PCT/JP2014/070702, dated Sep. 9, 2014.

*Primary Examiner* — Lisa M Caputo
*Assistant Examiner* — Philip L Cotey
(74) *Attorney, Agent, or Firm* — Arent Fox LLP

(57) ABSTRACT

A temperature and humidity sensor includes a substrate, a first electrode provided on the substrate, a linear second electrode at least part of which is so provided as to extend along the first electrode, and a moisture sensitive film provided between the part of the second electrode extending along the first electrode and the first electrode. The second electrode has a section that is formed in a spiral shape when viewed from above so as to form an inductor. With this, a precise oscillation circuit can be configured so that a temperature-humidity sensor small in size and capable of being easily manufactured can be provided.

14 Claims, 8 Drawing Sheets

(56) References Cited

U.S. PATENT DOCUMENTS

| | | | |
|---|---|---|---|
| 4,649,736 A * | 3/1987 | Austin | G01N 27/121 338/35 |
| 5,028,906 A * | 7/1991 | Moriya | G01N 27/121 338/35 |
| 5,767,687 A | 6/1998 | Geist | |
| 7,049,969 B2 * | 5/2006 | Tamai | A61F 13/42 340/572.4 |
| 2004/0089058 A1 | 5/2004 | de Haan et al. | |
| 2005/0008061 A1 * | 1/2005 | Kaneko | G01N 27/048 374/16 |
| 2006/0037393 A1 * | 2/2006 | Itakura | G01D 5/24 73/335.04 |
| 2007/0131020 A1 * | 6/2007 | Itakura | G01N 27/223 73/29.02 |
| 2007/0273394 A1 | 11/2007 | Tanner et al. | |
| 2008/0300559 A1 | 12/2008 | Gustafson et al. | |
| 2009/0056439 A1 * | 3/2009 | Suzuki | G01N 27/223 73/335.02 |
| 2009/0308155 A1 * | 12/2009 | Zhang | G01N 27/223 73/335.02 |
| 2010/0307238 A1 * | 12/2010 | Van Popta | G01N 27/225 73/335.04 |
| 2011/0259099 A1 | 10/2011 | Hong et al. | |
| 2013/0231620 A1 | 9/2013 | Thirstrup et al. | |

FOREIGN PATENT DOCUMENTS

| | | |
|---|---|---|
| JP | 6-148122 A | 5/1994 |
| JP | 07-020536 U | 4/1995 |
| JP | H07-20538 U | 4/1995 |
| JP | 11-056690 A | 3/1998 |
| JP | 2001-338827 A | 12/2001 |
| JP | 2008-628519 A | 6/2009 |
| JP | 2010-127927 A | 6/2010 |
| JP | 2012508877 A | 4/2012 |

* cited by examiner

TEMPERATURE AND HUMIDITY SENSOR

CROSS REFERENCE TO RELATED APPLICATIONS

The present application is a continuation of PCT/JP2014/070702 filed Aug. 6, 2014, which claims priority to Japanese Patent Application No. 2013-168039, filed Aug. 13, 2013, the entire contents of each of which are incorporated herein by reference.

FIELD OF THE INVENTION

The present invention relates to temperature and humidity sensors configured to detect temperatures and humidity.

BACKGROUND OF THE INVENTION

Temperature and humidity sensors capable of detecting temperatures and humidity are disclosed in, for example, Japanese Unexamined Utility Model Registration Application Publication No. 7-20536 (Patent Document 1), Japanese Unexamined Patent Application Publication No. 6-148122 (Patent Document 2), and Japanese Unexamined Patent Application Publication No. 58-70153 (Patent Document 3). These temperature and humidity sensors include a moisture sensitive film for humidity measurement and detect humidity based on a change in magnitude of resistance or electrostatic capacity.

Further, detection of electrostatic capacity of a humidity sensor using an oscillation circuit is disclosed in Japanese Unexamined Patent Application Publication No. 61-14556 (Patent Document 4) and Japanese Unexamined Patent Application Publication (Translation of PCT Application) No. 2012-508877 (Patent Document 5), for example.

Patent Document 1: Japanese Unexamined Utility Model Registration Application Publication No. 7-20536.

Patent Document 2: Japanese Unexamined Patent Application Publication No. 6-148122.

Patent Document 3: Japanese Unexamined Patent Application Publication No. 58-70153.

Patent Document 4: Japanese Unexamined Patent Application Publication No. 61-14556.

Patent Document 5: Japanese Unexamined Patent Application Publication (Translation of PCT Application) No. 2012-508877.

It can be considered to configure an oscillation circuit as disclosed in Patent Documents 4 and 5 using capacitance and resistance of a humidity sensor based on an electrostatic capacity technique as disclosed in Patent Documents 1 through 3 as well as inductance of an inductor that is provided separate from the humidity sensor.

In the case where an oscillation circuit is a CR oscillation circuit, because, in general, the phase rotation is gentle and oscillation frequency precision is low, and the circuit is susceptible to parasitic capacitance and resistance components, electrostatic capacity of a humidity sensor is required to be large. Accordingly, in a humidity sensor in which a moisture sensitive film is provided between two electrodes like the sensors in Patent Documents 1 and 2, areas of the electrodes need to be enlarged, thickness of the moisture sensitive film needs to be thinned, and so on. However, miniaturization of the sensor becomes difficult if the areas of the electrodes are enlarged, and an amount of change in electrostatic capacitance becomes small and the manufacturing of the sensor becomes difficult if the thickness of the moisture sensitive film is thinned. In a humidity sensor provided with linear electrodes like the sensor in Patent Document 3, intervals between the electrodes need to be narrowed. However, narrowing the intervals makes it difficult to manufacture the sensor.

SUMMARY OF THE INVENTION

An object of the present invention is to provide a temperature-humidity sensor that is small in size, easy to be manufactured, and capable of configuring a high-precision oscillation circuit.

The present invention provides a temperature and humidity sensor that includes a substrate, a first electrode provided on the substrate, a linear second electrode at least part of which is so provided as to extend along the first electrode, and a moisture sensitive film provided between the part of the second electrode extending along the first electrode and the first electrode. Further, the second electrode forms an inductor.

In one embodiment, the first electrode is formed of a first metal layer provided on the substrate. The moisture sensitive film is provided on the first metal layer. The second electrode includes spiral wiring and a signal lead-out wiring section. The spiral wiring is formed of a second metal layer provided on the moisture sensitive film and forms an inductor. The signal lead-out wiring section is formed of the first metal layer and three-dimensionally crosses the spiral wiring from a center portion toward an outer side portion of the spiral wiring.

In a further embodiment, the first electrode includes an electrode plate that is formed of the first metal layer and provided on the substrate in a region different from a region where the signal lead-out wiring section three-dimensionally crosses the spiral wiring.

In yet a further embodiment, the first electrode includes a wiring section that is formed of the first metal layer, provided on the substrate in a region different from the region where the signal lead-out wiring section three-dimensionally crosses the spiral wiring, and made to overlap with the spiral wiring.

In one embodiment, the second metal layer contains platinum or molybdenum.

In another embodiment, the first electrode is formed in a spiral shape when viewed from above and provided on the substrate. The second electrode is formed in a spiral shape when viewed from above and provided extending along the first electrode with a gap between the first electrode and the second electrode on the substrate. The moisture sensitive film is so provided on the substrate as to fill the gap between the first electrode and the second electrode.

According to the present invention, a miniaturized temperature and humidity sensor having high precision can be obtained.

DETAILED DESCRIPTION

Figure 1:
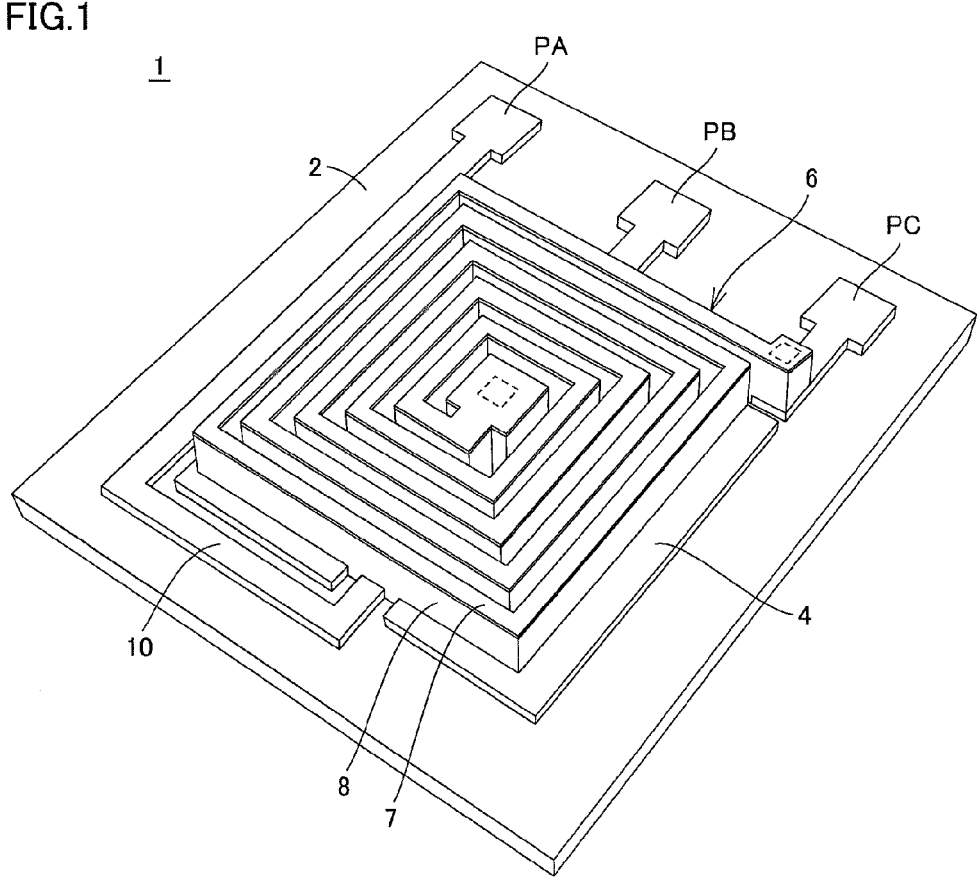
FIG. 1 is a perspective view illustrating a configuration of a temperature and humidity sensor according to a first embodiment.

Hereinafter, embodiments of the present invention will be described in detail with reference to the drawings. Note that the same reference numerals are given to identical or equivalent constituent elements in the drawings and descriptions thereof are not repeated.

First Embodiment

FIG. 1 is a perspective view illustrating a configuration of a temperature and humidity sensor according to a first embodiment.

Figure 2:
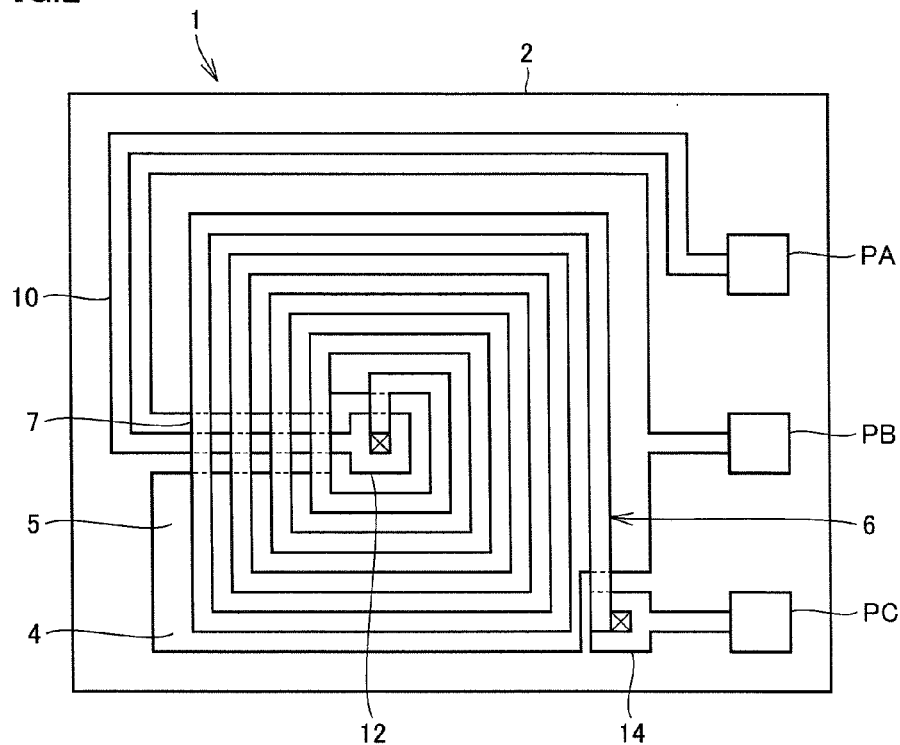
FIG. 2 is a plan view illustrating the configuration of the temperature and humidity sensor according to the first embodiment.

FIG. 2 is a plan view illustrating the configuration of the temperature and humidity sensor according to the first embodiment.

Referring to FIGS. 1 and 2, a temperature and humidity sensor 1 includes a substrate 2, a first electrode 4 provided on the substrate 2, a linear second electrode 6 at least part of which is so provided as to extend along the first electrode 4, and a moisture sensitive film 8 provided between the part of the second electrode 6 extending along the first electrode 4 and the first electrode 4. The second electrode 6 has a section that is formed in a spiral shape when viewed from above so as to form an inductor. Further, the temperature and humidity sensor 1 includes pads PA, PB, and PC.

The first electrode 4 is formed of a first metal layer provided on the substrate 2. The moisture sensitive film 8 is provided on the first metal layer. The second electrode 6 includes spiral wiring 7 and a signal lead-out wiring section 10. The spiral wiring 7 is formed of a second metal layer provided on the moisture sensitive film 8 and forms an inductor. The signal lead-out wiring section 10 is formed of the first metal layer and three-dimensionally crosses the spiral wiring 7 from a center portion toward an outer side portion of the spiral wiring 7. In other words, the signal lead-out wiring section 10 intersects with the spiral wiring 7 with the moisture sensitive film 8 interposed therebetween. One end portion of the spiral wiring 7 is connected to the pad PC, while the other end portion thereof is connected to the signal lead-out wiring section 10. One end portion of the signal lead-out wiring section 10 is connected to the pad PA, while the other end portion thereof is connected to the other end portion of the spiral wiring 7.

The first electrode 4 includes an electrode plate 5 formed of the first metal layer. The electrode plate 5 is provided on the substrate 2 in a region different from a region where the signal lead-out wiring section 10 three-dimensionally crosses the spiral wiring 7, and formed in a U shape in which an arrangement region of the signal lead-out wiring section 10 is recessed when viewed from above. Most of the spiral wiring 7 is provided on the electrode plate 5 with the moisture sensitive film 8 interposed therebetween. The electrode plate 5 is connected to the pad PB.

The second electrode 6 functions as both an inductor and a metallic resistor. Since a resistance value between the pads PA and PC connected to the second electrode 6 changes depending on a temperature, the temperature and humidity sensor 1 can also be used as a temperature sensor by detecting the resistance value between the pads PA and PC.

The substrate 2 is a silicon (Si) substrate on the surface of which a silicon dioxide ($SiO_2$) film is formed as an insulative film. The substrate 2 may be a dielectric substrate.

The first metal layer is formed of any one of gold (Au), aluminum (Al), copper (Cu), platinum (Pt), and molybdenum (Mo), or an alloy of any of these metals.

The moisture sensitive film 8 is formed of any one of photosensitive polyimide, porous silicon, and porous dielectric, and preferably formed of photosensitive polyimide.

The second metal layer is formed of any one of gold (Au), aluminum (Al), copper (Cu), platinum (Pt), and molybdenum (Mo), or an alloy of any of these metals. In the case where the temperature and humidity sensor 1 is used as a temperature sensor, it is preferable for the second metal layer to be formed of either platinum or molybdenum whose temperature coefficient of resistance is large.

It is particularly preferable for the moisture sensitive film 8 to be formed in a shape similar to that of the spiral wiring 7, as shown in FIG. 1. With this, the surface area of an exposed portion to the exterior of the moisture sensitive film 8 becomes large, whereby sensitivity can be enhanced as a humidity sensor.

Figure 3:
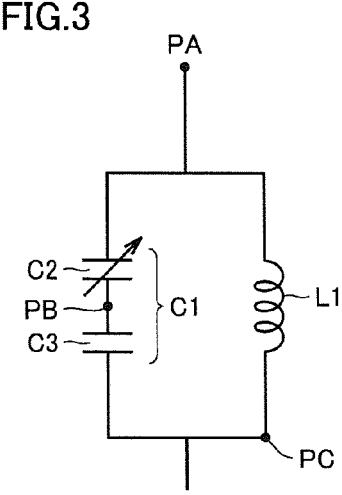
FIG. 3 is an equivalent circuit diagram of the temperature and humidity sensor according to the first embodiment.

FIG. 3 is an equivalent circuit diagram of the temperature and humidity sensor 1 according to the first embodiment.

Referring to FIGS. 2 and 3, an inductor L1 corresponds to the inductor formed of inductance of the spiral wiring 7. Further, a variable capacitor C2 is configured including the moisture sensitive film 8 as a dielectric and the first electrode 4 and the second electrode 6 opposing each other with the moisture sensitive film 8 interposed therebetween. Nodes PA, PB, and PC in FIG. 3 electrically correspond to the pads PA, PB, and PC in FIG. 2, respectively. Connecting a capacitor C3 between the pads PA and PC prevents DC direct-connection. Note that the capacitor C3 is prepared separate from the temperature and humidity sensor 1. The variable capacitor C2 and the capacitor C3 configure a capacitor C1.

Figure 4:
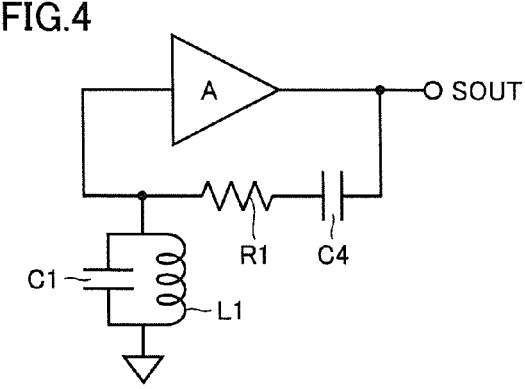
FIG. 4 is a circuit diagram of an oscillation circuit into which a temperature and humidity sensor is integrated.

FIG. 4 is a circuit diagram of an oscillation circuit into which the temperature and humidity sensor 1 according to the first embodiment is integrated. A parallel connection portion of the capacitor C1 and the inductor L1 of a resonance circuit shown in FIG. 4 corresponds to the circuit shown in FIG. 3. Note that, however, the temperature and humidity sensor 1 is configured as a three-terminal element having the pads PA, PB, and PC without directly connecting the pads PB and PC to be used not only in the resonance circuit shown in FIG. 4 (tank circuit) but also in a resonance circuit of a CL series resonance type.

Variation on First Embodiment

Figure 5:
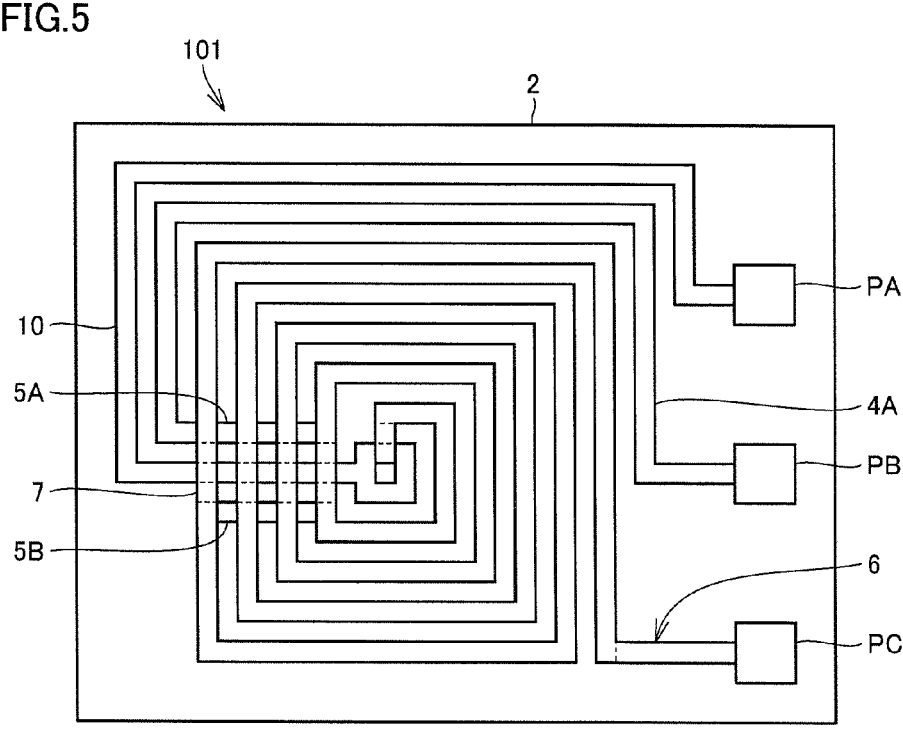
FIG. 5 is a plan view illustrating a configuration of a temperature and humidity sensor according to a variation on the first embodiment.

FIG. 5 is a plan view illustrating a configuration of a temperature and humidity sensor 101 according to a variation on the first embodiment.

Figure 6:
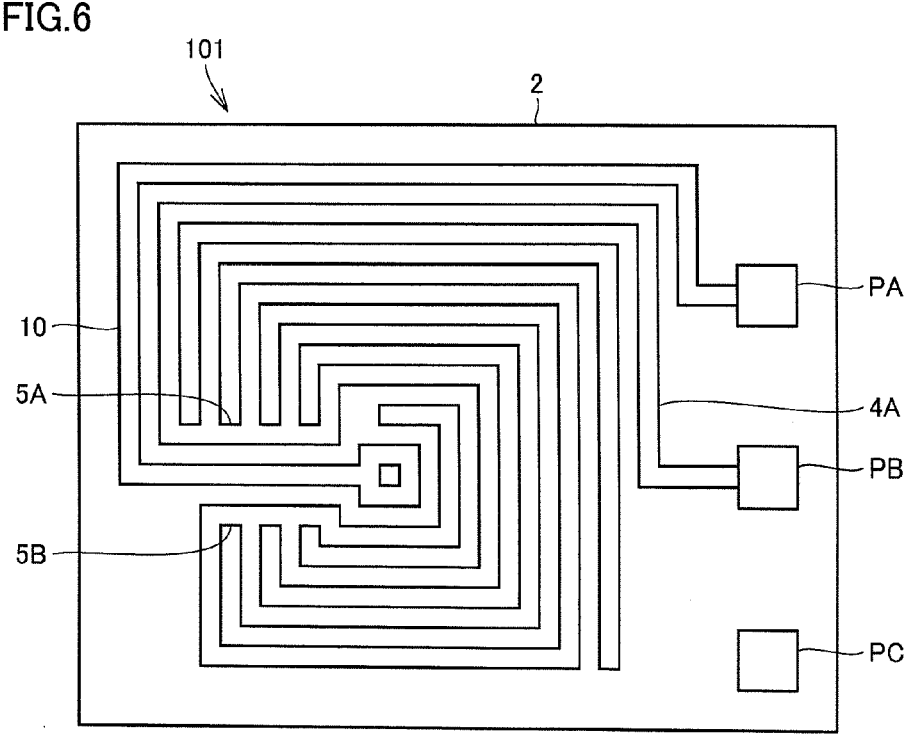
FIG. 6 is a diagram in which spiral wiring in FIG. 5 is removed to explain the shape of a first electrode.

FIG. 6 is a diagram in which spiral wiring in FIG. 5 is removed to explain the shape of a first electrode.

Referring to FIGS. 5 and 6, the temperature and humidity sensor 101 according to the variation on the first embodiment includes a first electrode 4A in place of the first electrode 4 in the configuration of the temperature and humidity sensor 1 shown in FIG. 2. The first electrode 4 in FIG. 2 is provided on the substrate 2 in a region different from the region where the signal lead-out wiring section 10 three-dimensionally crosses the spiral wiring 7, and includes the electrode plate 5 formed in a U shape when viewed from above. Meanwhile, instead of the electrode plate 5, the first electrode 4A includes a wiring section formed in a shape substantially similar to that of the spiral wiring 7 and connection wiring sections 5A and 5B configured to connect adjacent wiring portions to each other. In other words, the wiring section of the first electrode 4A overlaps with the spiral wiring 7 when viewed from above.

With this configuration, a miniaturized temperature and humidity sensor having high precision can also be obtained like the temperature and humidity sensor 1 shown in FIG. 2.

Figure 7:
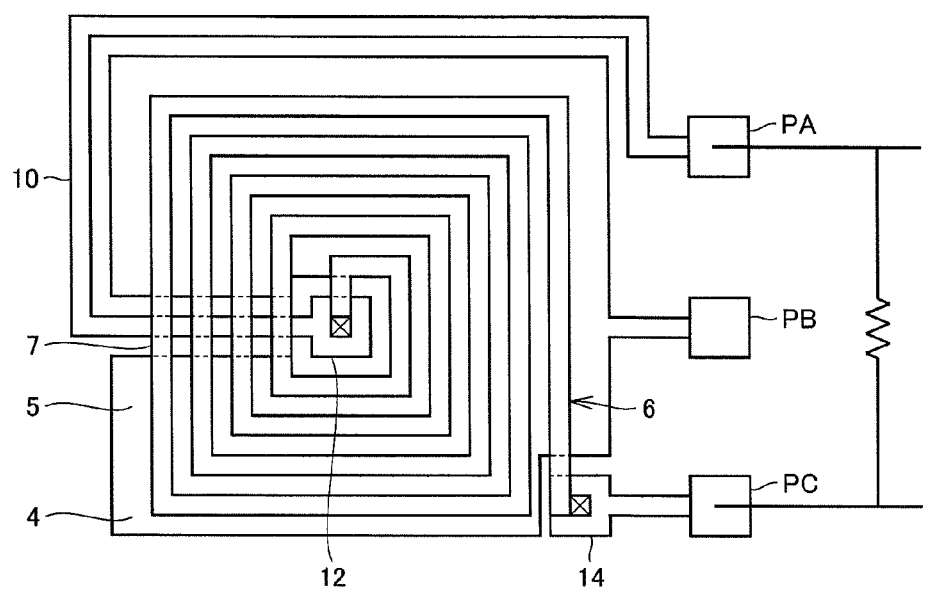
FIG. 7 is a diagram for explaining use of a temperature and humidity sensor as a temperature sensor.

Next, a function as a temperature sensor will be described. FIG. 7 is a diagram for explaining use of the temperature and humidity sensor 1 shown in FIG. 2 as a temperature sensor. The signal lead-out wiring section 10 and the spiral wiring 7 are connected between the pads PA and PC. Accordingly, a resistance value of the signal lead-out wiring section 10 and the spiral wiring 7 is approximately equal to a resistance value between the pads PA and PC.

Figure 8:
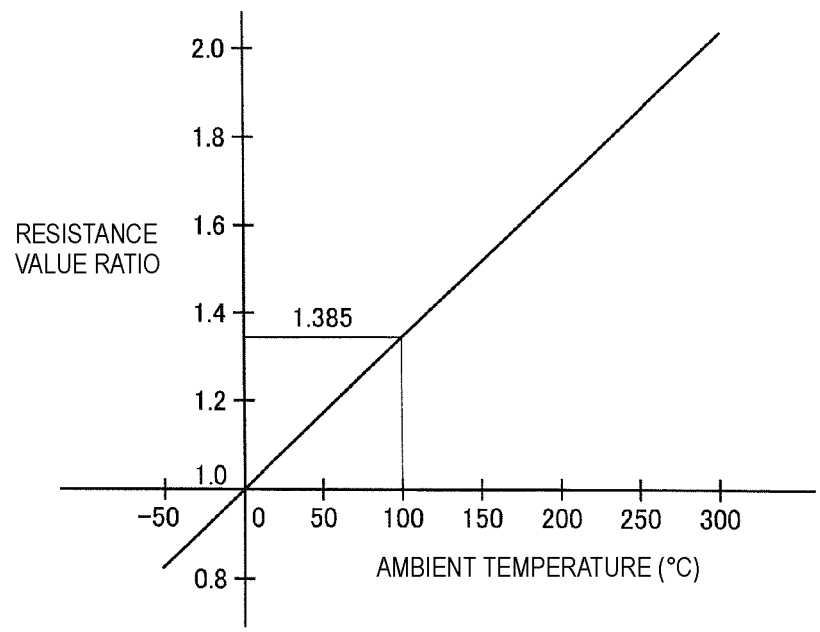
FIG. 8 is a graph illustrating a relationship between a resistance value of a temperature and humidity sensor 1 and temperature.

FIG. 8 is a graph illustrating a relationship between a resistance value of the temperature and humidity sensor 1 in which the second metal layer is made of platinum and temperature. In order to use the temperature and humidity sensor 1 as a temperature sensor, it is preferable to use platinum as the second metal layer that forms the spiral wiring 7. In this case, as shown in FIG. 8, a change in an ambient temperature and a resistance value ratio exhibits a favorable linearity.

Second Embodiment

Figure 9:
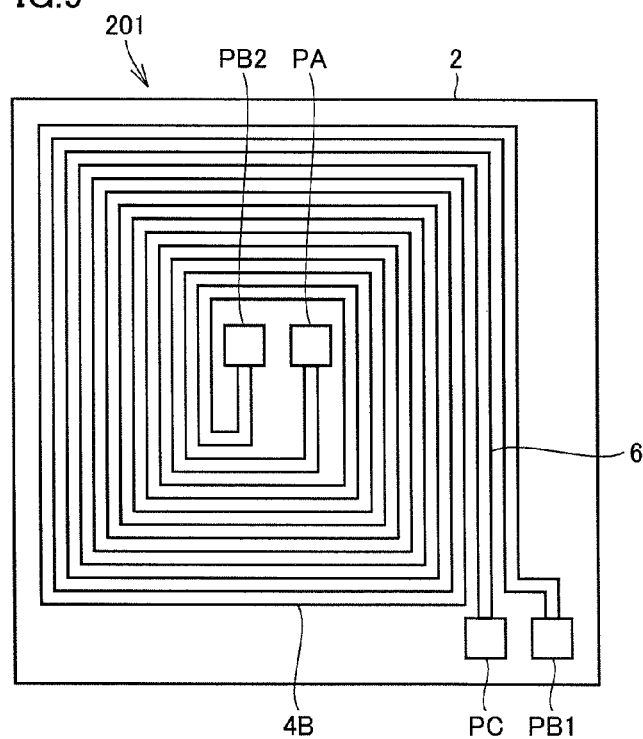
FIG. 9 is a plan view illustrating a configuration of a temperature and humidity sensor according to a second embodiment.
Figure 10:
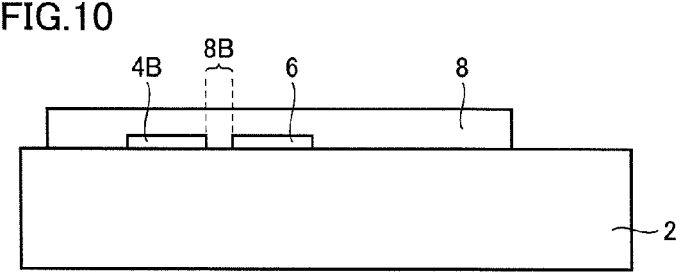
FIG. 10 is a schematic cross-sectional view of the temperature and humidity sensor according to the second embodiment.
Figure 11:
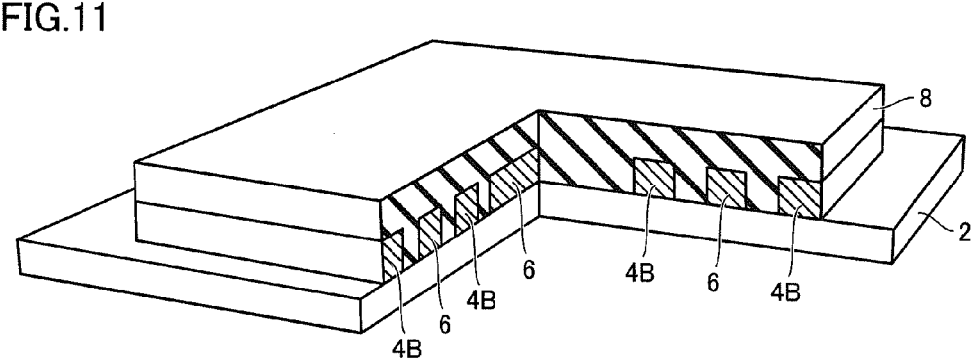
FIG. 11 is a perspective view illustrating a schematic cross section of the temperature and humidity sensor according to the second embodiment.

FIG. 9 is a plan view illustrating a configuration of a temperature and humidity sensor according to a second embodiment. FIG. 10 is a schematic cross-sectional view of the temperature and humidity sensor according to the second embodiment. FIG. 11 is a perspective view illustrating a schematic cross section of the temperature and humidity sensor according to the second embodiment.

Referring to FIGS. 9 and 10, a temperature and humidity sensor 201 includes the substrate 2, a first electrode 4B provided on the substrate 2, the linear second electrode 6 at least part of which is so formed as to extend along the first electrode 4B, and the moisture sensitive film 8 part of which is provided between the first electrode 4B and the second electrode 6 opposing each other. The second electrode 6 is formed in a spiral shape when viewed from above so as to form an inductor.

The first electrode 4B is formed in a spiral shape when viewed from above and provided on the substrate 2. The second electrode 6 is formed in a spiral shape when viewed from above and provided extending along the first electrode 4B with a gap between the first electrode 4B and the second electrode 6 on the substrate 2. The moisture sensitive film 8 is so provided on the substrate 2 as to fill the gap between the first electrode 4B and the second electrode 6 with a portion 8B as shown in FIG. 11. In the present embodiment, the first electrode 4B and the second electrode 6 are covered by the moisture sensitive film 8. One end portion of the first electrode 4B is connected to a pad PB1, while the other end portion thereof is connected to a pad PB2. One end portion of the second electrode 6 is connected to the pad PC, while the other end portion thereof is connected to the pad PA.

In the temperature and humidity sensor 1 according to the first embodiment, most of the spiral wiring 7 is provided on the electrode plate 5 with the moisture sensitive film 8 interposed therebetween, and the electrode plate 5 of the first electrode 4 opposes most of the spiral wiring 7 of the second electrode 6 in a normal direction of the substrate 2 with the moisture sensitive film 8 interposed therebetween. As shown in FIGS. 10 and 11, in the temperature and humidity sensor 201 according to the second embodiment, the first electrode 4B and the second electrode 6 are provided to be at the same plane level on the substrate 2, that is, provided having the same height from the substrate 2. This makes the first electrode 4B and the second electrode 6 oppose each other in a direction parallel to the substrate 2. It is preferable for the first electrode 4B and the second electrode 6 to be formed by etching, using a photolithographic technique, the metal layers formed in the same process.

Figure 12:
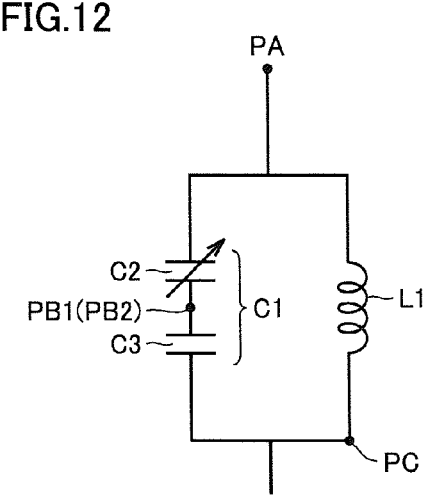
FIG. 12 is an equivalent circuit diagram of the temperature and humidity sensor according to the second embodiment.

FIG. 12 is an equivalent circuit diagram of the temperature and humidity sensor 201 according to the second embodiment. Although the circuit diagram shown in FIG. 12 is basically the same as the circuit diagram described in FIG. 3, it differs from the circuit diagram in FIG. 3 in that the pad PB1 or PB2 is indicated as corresponding to a connection node of the capacitor C1 and the capacitor C2. It is sufficient to connect the capacitor C3 between the pad PB1 or PB2 and the pad PC at the outside of the temperature and humidity sensor 201. In this case, the pads PB1 and PB2 may be connected with external wiring so as to lower the resistance.

Since the above-described circuit is applied to the oscillation circuit shown in FIG. 4 in the same manner as discussed before, the description thereof is not repeated herein.

Figure 13:
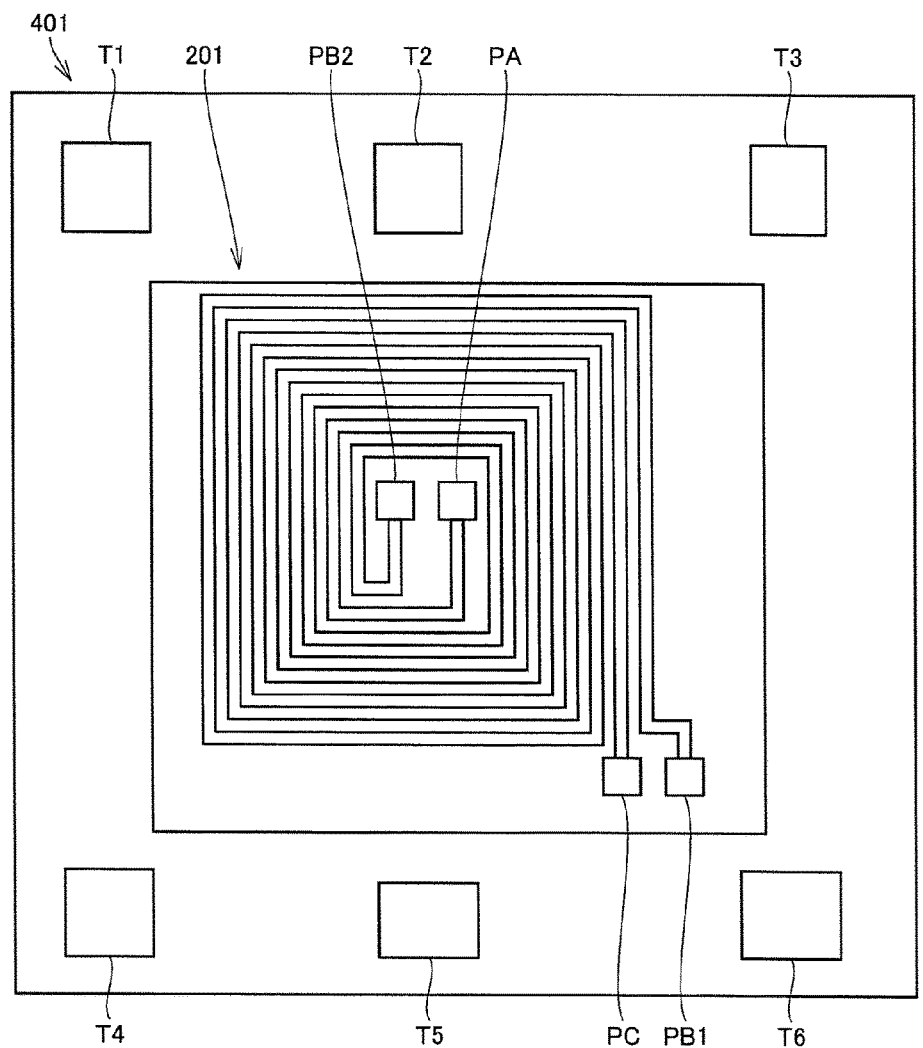
FIG. 13 is a diagram illustrating a device shape in which the temperature and humidity sensor according to the second embodiment is mounted on an IC.

FIG. 13 is a diagram illustrating a device shape in which the temperature and humidity sensor 201 according to the second embodiment is mounted on an IC 401. As the IC 401, a CMOS-ASIC for detection that configures an oscillation circuit is used. As shown in FIG. 13, external terminals T1 through T6 are disposed on the periphery of the temperature and humidity sensor 201, and the temperature and humidity sensor 201 is disposed in a center portion of the IC 401.

Variation on Second Embodiment

Figure 14:
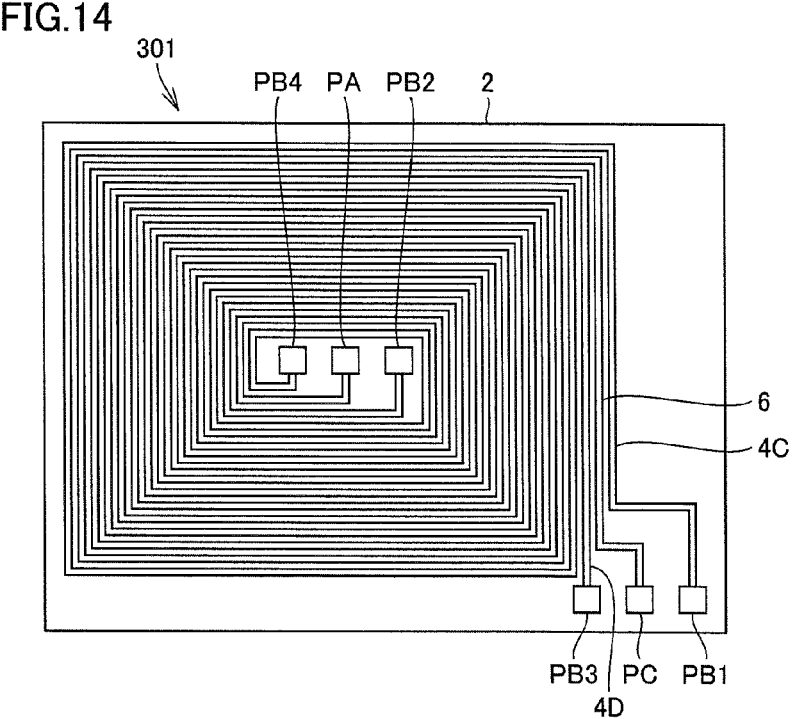
FIG. 14 is a plan view illustrating a configuration of a temperature and humidity sensor according to a variation on the second embodiment.
Figure 15:
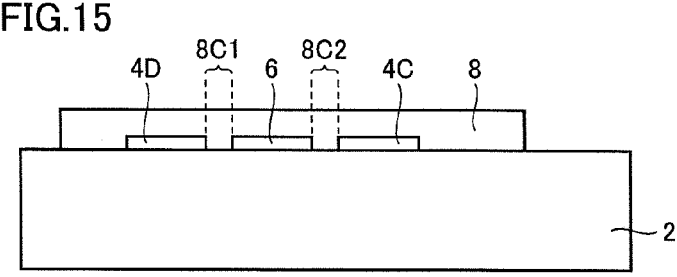
FIG. 15 is a schematic cross-sectional view of the temperature and humidity sensor according to the variation on the second embodiment.

FIG. 14 is a plan view illustrating a configuration of a temperature and humidity sensor 301 according to a variation on the second embodiment. FIG. 15 is a schematic cross-sectional view of the temperature and humidity sensor 301 according to the variation on the second embodiment. In the configuration shown in FIGS. 14 and 15, a first electrode 4C and a first electrode 4D are respectively provided on both sides of the second electrode 6.

The first electrodes 4C and 4D are each formed in a spiral shape when viewed from above, and provided on the substrate 2. The second electrode 6 is formed in a spiral shape when viewed from above, and provided extending along the first electrodes 4C and 4D with gaps between the second electrode 6 and both the first electrodes 4C and 4D, respectively, on the substrate 2. The moisture sensitive film 8 is so provided on the substrate 2 as to fill the gap between the first electrode 4C and the second electrode 6 with a portion 8C2 as shown in FIG. 15 and also fill the gap between the first electrode 4D and the second electrode 6 with a portion 8C1. In the present embodiment, the first electrodes 4C, 4D and the second electrode 6 are covered by the moisture sensitive film 8. One end portion of the first electrode 4C is connected to the pad PB1, while the other end portion thereof is connected to the pad PB2. One end portion of the first electrode 4D is connected to a pad PB3, while the other end portion thereof is connected to a pad PB4. One end portion of the second electrode 6 is connected to the pad PC, while the other end portion thereof is connected to the pad PA.

As shown in FIGS. 14 and 15, in the temperature and humidity sensor 301 according to the variation on the second embodiment, the first electrodes 4C, 4D and the second electrode 6 are provided to be at the same plane level on the substrate 2, that is, provided having the same height from the substrate 2. This makes the first electrodes 4C, 4D and the second electrode 6 oppose one another in a direction parallel to the substrate 2.

The first electrode 4C and the first electrode 4D may be used as an inductor, and the second electrode 6 may be used as a capacitor.

A miniaturized temperature and humidity sensor having high precision can also be obtained by using the temperature and humidity sensor 301 according to the variation on the second embodiment like the temperature and humidity sensor 201 according to the second embodiment.

In other words, two or more electrodes configuring an inductor are provided on the substrate 2, and a moisture sensitive film is so provided as to cover the electrodes. A resistance value between input and output of the electrodes serves as a temperature sensor. That is, the electrodes function as both an inductor and a metallic resistor.

In particular, in the case of using a silicon substrate where an oscillation circuit, constituent elements of a digital circuit, and so on are included in the substrate, a temperature and humidity sensor can be manufactured through such a simple process that the electrodes are formed, for example, by a CMOS semiconductor process to form the moisture sensitive film by spin coating.

It should be noted that the embodiments disclosed in the present specification are merely examples in all aspects and not limiting in any way. The range of the present invention is determined not by the aforementioned descriptions but by the appended claims, and is intended to include meanings equivalent to the appended claims as well as all the modifications carried out within the range of the present invention.

REFERENCE SIGNS LIST 1, 101, 210 TEMPERATURE AND HUMIDITY SENSOR
2 SUBSTRATE
4, 4A, 4B, 4C, 4D FIRST ELECTRODE
5 ELECTRODE PLATE
5A, 5B CONNECTION WIRING SECTION
6 SECOND ELECTRODE
7 SPIRAL WIRING
8 MOISTURE SENSITIVE FILM
10 SIGNAL LEAD-OUT WIRING SECTION
C1, C2, C3 CAPACITOR
L1 INDUCTOR
PA, PB, PC PAD
T1-T6 EXTERNAL TERMINAL

The invention claimed is:

1. A sensor comprising:
a substrate;
a pair of first electrodes disposed directly on a first surface of the substrate, with each of the pair of first electrodes comprising a spiral shape in a plan view of the substrate;
a moisture sensitive film disposed between the pair of electrodes and that covers the pair of first electrodes; and
a linear second electrode having at least a portion thereof extending along at least a portion of at least one of the pair of first electrodes; and
wherein the linear second electrode is disposed above a portion of the moisture sensitive film and the portion of the linear second electrode extends along the portion of the at least one of the pair of first electrodes, and
wherein the linear second electrode is separated from the pair of first electrodes by the moisture sensitive film, and
wherein the moisture sensitive film comprises a shape corresponding to a shape of the linear second electrode, such that an exposed surface area of the moisture sensitive film is configured to increase sensitivity of the sensor.

2. The sensor according to claim 1, wherein the second electrode comprises a shape such that the second electrode is configured as an inductor.

3. The sensor according to claim 1, wherein
at least one of the pair of first electrode is formed of a first metal layer disposed on the substrate, and
the second electrode includes spiral wiring and a signal lead-out wiring section.

4. The sensor according to claim 3, wherein the spiral wiring is formed of a second metal layer and is disposed on the moisture sensitive film.

5. The sensor according to claim 4, wherein the signal lead-out wiring section is formed of the first metal layer and crosses the spiral wiring from a center portion of the spiral wiring towards a side portion of the spiral wiring.

6. The sensor according to claim 5, wherein the at least one electrode of the pair of first electrodes includes a wiring section that is formed of the first metal layer, and the wiring section is disposed on the substrate in a region different from a region where the signal lead-out wiring section crosses the spiral wiring.

7. The sensor according to claim 6, wherein the wiring section is disposed to overlap with the spiral wiring.

8. The sensor according to claim 3, wherein the second metal layer comprises platinum or molybdenum.

9. The sensor according to claim 3, wherein the signal lead-out wiring section extends through an opening of one of the pair of first electrodes.

10. The sensor according to claim 1, wherein the second electrode comprises a spiral shape in a plan view of the substrate and is disposed extending along the first electrode with a gap between the first electrode and the second electrode on the substrate.

11. The sensor according to claim 1, wherein the second electrode comprises a spiral shape in a plan view of the substrate and is disposed between the pair of first electrodes.

12. The sensor according to claim 11, wherein the moisture sensitive film is disposed on the substrate to fill a gap between the pair of first electrodes and the second electrode.

13. The sensor according to claim 12, wherein the moisture sensitive film covers the pair of first electrodes and the second electrode.

14. The sensor according to claim 1, wherein the moisture sensitive film is disposed on the pair of first electrodes with the moisture sensitive film being disposed between the pair of first electrodes and the portion of the second electrode extending along the portion of the first electrode, such that the pair of first electrodes, the moisture sensitive film and the linear second electrode are layered relative to a thickness direction of the sensor.

* * * * *